(12) United States Patent
Junk et al.

(10) Patent No.: US 7,834,209 B2
(45) Date of Patent: Nov. 16, 2010

(54) HYDROFLUOROALKANESULFONIC ACIDS FROM FLUOROVINYL ETHERS

(75) Inventors: Christopher P. Junk, Wilmington, DE (US); Mark Andrew Harmer, Kennett Square, PA (US); Andrew Edward Feiring, Wilmington, DE (US); Frank Leonard Schadt, III, Wilmington, DE (US); Zoe Schnepp, Beech Hill (GB)

(73) Assignee: E.I. du Pont de Nemours and Company, Wilmington, DE (US)

( * ) Notice: Subject to any disclaimer, the term of this patent is extended or adjusted under 35 U.S.C. 154(b) by 621 days.

(21) Appl. No.: 11/447,825

(22) Filed: Jun. 6, 2006

(65) Prior Publication Data

US 2006/0276670 A1    Dec. 7, 2006

Related U.S. Application Data

(60) Provisional application No. 60/688,228, filed on Jun. 7, 2005, provisional application No. 60/688,095, filed on Jun. 7, 2005.

(51) Int. Cl.
*C07C 309/02* (2006.01)
*C07C 315/00* (2006.01)

(52) U.S. Cl. .................. 562/111; 562/108; 562/109; 568/28; 568/34; 568/35

(58) Field of Classification Search .............. 562/108, 562/109, 111
See application file for complete search history.

(56) References Cited

U.S. PATENT DOCUMENTS

| | | | |
|---|---|---|---|
| 3,282,875 | A | 11/1966 | Connolly et al. |
| 4,138,426 | A | 2/1979 | England |
| 4,538,545 | A | 9/1985 | English et al. |
| 4,897,457 | A | 1/1990 | Nakamura et al. |
| 4,940,525 | A | 7/1990 | Ezzell et al. |
| 4,982,009 | A | 1/1991 | Hung |
| 5,196,569 | A | 3/1993 | Hung |
| 5,260,492 | A | 11/1993 | Feiring et al. |
| 5,372,912 | A | 12/1994 | Allen et al. |
| 5,637,748 | A | 6/1997 | Hung et al. |
| 5,654,121 | A * | 8/1997 | Eichhorn et al. ............ 430/157 |
| 5,969,067 | A | 10/1999 | Brothers et al. |
| 6,358,665 | B1 * | 3/2002 | Pawlowski et al. ....... 430/270.1 |
| 2006/0197053 | A1 * | 9/2006 | Shiflett et al. ................. 252/67 |
| 2007/0019708 | A1 * | 1/2007 | Shiflett et al. ............... 374/181 |

FOREIGN PATENT DOCUMENTS

| | | |
|---|---|---|
| JP | 2005-148291 | 6/2005 |
| JP | 2005-258124 | 9/2005 |
| WO | WO 97/33198 | 9/1997 |
| WO | WO 00/17712 | 3/2000 |
| WO | WO 00/25178 | 5/2000 |
| WO | WO 02/082185 A1 | 10/2002 |
| WO | WO 2006/084262 A1 | 8/2006 |

OTHER PUBLICATIONS

Willson, C. G., "Organic Resist Materials"; Introduction to Microlithography, Second Edition by L. F, Thompson, C. G. Willson, and M. J. Bowden, American Chemical Society, Washington, DC, 1994, Chapter 3.
Houlihan, F. M., et al, Synthesis of Cycloolefin—Maleic Anhydride Alternating Copolymers FRO 193 NM Imaging, Macromolecules, 30, pp. 6517-6534 (1997).
Wallow, T. I., et al, "Evaluation of Cycloolefin-Maleic Anhydride Alternating Copolymers as Single-Layer Photoresists for 193 NM Photolithography", Proc. SPIE, 2724, 335 (1996).
Houlihan, F. M., et al, "A Commercially Viable 193 NM Single Layer Resist Platform", Journal of Photopolymer Science and Technology, 10, 511 (1997).
Okoroanyanwu, U., et al, PD(II)-Catalyzed Addition Polymerization and Ring Opening Metathesis Polymerization of Alicyclic Monomers: Routes to New Matrix Resins for 193 NM Photolithography, J. Mol. Cat. A: Chemical 133, 93 (1998).
Przybilla, K. J., et al, "Hexafluoroacetone in Resist Chemistry: A Versatile New Concept for Materials for Deep UV Lithography", Proc. SPIE 1672, 9 (1992).
Ito, H., et al, "Synthesis and Preliminary Evaluation of Substituted Poly (Norbornene Sulfones) for 193 NM Lithography", Polymn. Mater. Sci. Eng. 77, 449 (1997).
Reichmanis, E., et al, "The Effect of Substituents on the Photosensitivity of 2-Nitrobenzyl Ester Deep U.V. Resists", J. Electrochem. Soc., vol. 130, No. 6, pp. 1433-1437 (1983).
M. B. Shiflett, et al., "Solubility and diffusivity of difluoromethane in room-temperature ionic liquids", Journal of Chemical and Engineering Data, vol. 51, No. 2, Jan. 27, 2006, pp. 483-495, American Chemical Society, Washington, D.C.

* cited by examiner

*Primary Examiner*—Porfirio Nazario Gonzalez
*Assistant Examiner*—Yate' K Cutliff

(57) ABSTRACT

Hydrofluoroalkanesulfonates of the general formula R—O—CXH—CX$_2$—SO$_3$M, where R is selected from the group consisting of alkyl groups, functionalized alkyl groups, and alkenyl groups; X is selected from the group consisting of hydrogen and fluorine with the proviso that at least one X is fluorine; and M is a cation, are made by reacting fluorovinyl ether with aqueous sulfite solution. Organic onium hydrofluoroalkanesulfonates are useful as ionic liquids and photoacid generators.

9 Claims, No Drawings

HYDROFLUOROALKANESULFONIC ACIDS FROM FLUOROVINYL ETHERS

BACKGROUND OF THE INVENTION

1. Field of the Invention.

This invention is in the field of strong acids useful for catalysis, and their salts.

2. Description of Related Art

Trifluoromethanesulfonic acid (TFMSA) is used for catalysis where a strong acid is needed. It offers a safer, more easily handled alternative to the inorganic acids, hydrogen fluoride and sulfuric acid, which are widely used in industrial processes. In addition, because of its low molecular weight, trifluoromethanesulfonic acid is relatively volatile, a disadvantage in high temperature processes. Known hydrofluoroalkanesulfonic acids, such as 1,1,2,2-tetrafluoroethanesulfonic acid (TFESA) and 1,1,2,3,3,3-hexafluoropropanesulfonic acid (HFPSA), are made from tetrafluoroethylene and hexafluoropropylene, respectively, and are somewhat higher in molecular weight and therefore have lower volatility, but for still less volatile hydrofluoroalkanesulfonic acids higher molecular weight fluoroolefins would be needed. There are few such fluoroolefins of commercial importance and consequently of ready availability.

Furthermore, salts of TFMSA have utility as photoacid generators and ionic liquids. Those having a photoactive cationic moiety are useful photoacid generators for microlithography. In the process of microlithography, molecules called "photoacid generators" (PAGs) are used to capture photons of light and generate protons. The PAG plays an important role in the imaging process for both positive- and negative-working chemically amplified resists, because the PAG governs light response properties, such as absorption of light or quantum yield of acid formation. In addition, the PAG governs the properties of the produced acid, such as acid strength, mobility, and volatility.

Useful PAGs include organic onium salts, e.g., iodonium salts and sulfonium salts, with non-nucleophilic anions. Organic onium salts producing trifluoromethane sulfonic acids upon exposure have been particularly preferred, because superior sensitivity and good ultimate resolution of the photoresist system can be obtained. In addition, these PAGs are known to reduce the formation of insolubles ("scum") on the substrate or at the substrate/resist interface. A known drawback of such PAGs is that minor quantities of the rather volatile trifluoromethanesulfonic acid (TFSA) produced during the irradiation process may evaporate (outgas) from the photoresist film and cause corrosion of the exposure and process equipment. In addition, it is known that resist materials containing PAGs that produce TFSA tend to produce the so-called T-shaped pattern profiles, and show linewidth changes upon process delays due to the high volatility and the diffusion properties of this acid.

In summary, the minor quantities of TFMSA produced from the salt can outgas, causing corrosion to process equipment. Volatility is also related to the rate of diffusion of the acid. Diffusion is an undesirable property in microlithography.

U.S. Pat. No. 6,358,665 discloses onium salt precursors, Y+ASO3−, which generate a fluorinated alkanesulfonic acid. Y represents $(R^1)(R^2)(R^3)S^+$ or $(R^4)(R^5)I^+$ and A represents CF3CHFCF2 or CF3CF2CF2CF2.

WO 02/082185 discloses photoacid compounds with the general structure $R—O(CF_2)_nSO_3X$, where n is an integer between about 1 to 4; X is selected from the group consisting of organic cations and covalently bonded organic radicals; and suitable R groups include substituted or unsubstituted C1-C12 linear or branched alkyl groups and substituted or unsubstituted perfluoroalkyl groups.

There is a need for hydrofluoroalkanesulfonates and hydrofluoroalkanesulfonic acids of higher molecular weight, for use in catalysis, in ionic liquids and in photoacid generators. It would be particularly advantageous for such hydrofluoroalkanesulfonates to be preparable from readily available starting materials.

BRIEF SUMMARY OF THE INVENTION

The present invention provides hydrofluoroalkanesulfonates of the general formula $R—O—CXH—CX_2—SO_3M$, where R is selected from the group consisting of alkyl groups, functionalized alkyl groups, and alkenyl groups; X is selected from the group consisting of hydrogen and fluorine with the proviso that at least one X is fluorine; and M is a cation.

The present invention also provides a process for manufacture of hydrofluoroalkanesulfonates of the general formula $R—O—CXH—CX_2—SO_3M$, where R is selected from the group consisting of alkyl groups, functionalized alkyl groups, and alkenyl groups; X is selected from the group consisting of hydrogen and fluorine with the proviso that at least one X is fluorine; and M is a cation, comprising contacting a vinyl ether of the formula $R—O—CX=CX_2$, with sulfite in an aqueous solution adjusted to about pH 4 to pH 12, and recovering the hydrofluoroalkanesulfonate. In accordance with a preferred aspect of the of the invention, the hydrofluoroalkanesulfonate is reacted with acid when the hydrofluoroalkanesulfonic acid is desired as the final product. Preferably this is accomplished by recovering the hydrofluoroalkanesulfonate from the aqueous solution containing hydrofluoroalkanesulfonate as a solid, treating the solid with oleum, and distilling hydrofluoroalkanesulfonic acid therefrom.

The invention also provides a compound of the formula $R—O—CXH—CX_2—SO_3M$, where R is selected from the group consisting of alkyl groups, functionalized alkyl groups, and alkenyl groups; X is selected from the group consisting of hydrogen and fluorine with the proviso that at least one X is fluorine; and M is organic onium. Compounds in accordance with this form of the invention are useful as ionic liquids and photoacid generators.

DETAILED DESCRIPTION OF THE INVENTION

It has been discovered that fluorovinyl ethers of the general formula $CF_2=CF—OR$, react with aqueous sulfite to yield hydrofluoroalkanesulfonates. The reaction, represented as the reaction of a perfluorovinyl ether with sulfite, is:

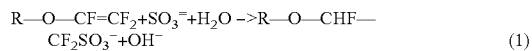

(1)

Though (1) is the principal adduct, the hydration reaction (2) is also seen in minor amount (0.1-3%).

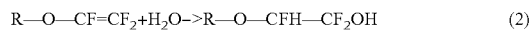

(2)

The hydration product in (2) further hydrolyzes to form the carboxylic acid:

(3)

R represents: (A) alkyl. Alkyl means hydrocarbon group, which may be substituted with halogen and, if so substituted, preferably the halogen is fluorine or chlorine, preferably alkyl is fluoroalkyl, and more preferably is perfluoroalkyl. Alkyl may be linear or branched, or cyclic. Preferably, alkyl is linear alkyl. The alkyl group R may contain one or more ether linkages. Preferably, the alkyl group has 1 to 20 carbon atoms. These fluorovinyl ethers are preferably trifluoro(alkyl vinyl ethers). Preferred fluorovinyl ethers are perfluoro(alkyl vinyl ethers) (PAVE) such as perfluoro(methyl vinyl ether) (PMVE), perfluoro(ethyl vinyl ether) (PEVE), and perfluoro (propyl vinyl ether) (PPVE). Members of this class of fluorovinyl ethers are referred to herein as nonfunctional fluorovinyl ethers.

R also represents: (B) a functionalized alkyl group, i.e., an alkyl group as defined above which contains a functional group. By functional group is meant a group that confers, or is capable of conferring, such as after hydrolysis or other treatment, significant reactivity, such as ionic character, hydrogen-bonding character, or strongly polar character, such as dipolar character. By strongly polar is meant polarity greater than that of carbon-hydrogen, or carbon-halogen bonds. Examples of such functional groups are hydroxyl (—OH) or —$CH_2OH$; carboxyl (—$COO^-$) including carboxylic ester, amide, acid, or salt; sulfonate (—$SO_3^-$) including sulfonyl halide, preferably fluoride, sulfonic acid, sulfonamide, or sulfonate salt; phosphonate (—$P(O)O_2^-$), including phosphonic acid or salt; cyanide (—CN). Other possible functional groups are glycidyl, cyanate (—OCN) and carbamate (—O—NH—R'), where R' is an alkyl group, preferably methyl, with the understanding that such groups may undergo partial or complete hydrolysis under the conditions of the reaction with sulfite. These fluorovinyl ethers are preferably trifluoro(alkyl vinyl ethers). Apart from the functional group(s), these functional fluorovinyl ethers are preferably perfluorovinyl ethers, i.e., R' is perfluorinated. Members of this class of fluorovinyl ethers are referred to herein as functional fluorovinyl ethers.

Preferred classes of functional vinyl ethers are:

$CF_2$=CF—($OCF_2CF(CF_3)$)$_n$(O)$_p$($CF_2$)$_m$—Z, where p is 0 or 1, m is 0 to 10 and n is 1 to 20, provided that when m is 0, p is 0, and further provided that when m is greater than 0, p is 1, and Z is a functional group such as —$CH_2OH$, carboxyl (—$COO^-$) including carboxylic ester, amide, acid, or salt; sulfonate (—$SO_3^-$) including sulfonyl halide, preferably fluoride, sulfonic acid, sulfonamide, or sulfonate salt; phosphonate (—O—$P(O)O_2^-$), including phosphonic acid, acid halide, or salt; glycidyl; cyanide (—CN); cyanate, and carbamate.

$CF_2$=CF—O—Y—$CF_2$—Z, where Y is alkylene, preferably fluoroalkylene, and more preferably perfluoroalkylene and may be cyclic and may include one or more ether oxygens, and is most preferably $CF_2$, and Z is a functional group such as —$CH_2OH$, carboxyl (—$COO^-$) including carboxylic ester, amide, acid, or salt; sulfonate (—$SO_3^-$) including sulfonyl halide, preferably fluoride, sulfonic acid, sulfonamide, or sulfonate salt; phosphonate (—O—$P(O)O_2^-$), including phosphonic acid, acid halide, or salt; glycidyl; cyanide (—CN); cyanate, and carbamate.

Examples of such functional vinyl ethers from the patent literature are found in U.S. Pat. Nos. 3,282,875; 4,138,426; 4,538,545; 4,940,525; 4,982,009; 5,196,569; 5,637,748; 5,866,711; and 5,969,067.

Preferred embodiments of functional vinyl ethers include:

$CF_2$=CF—O—$CF_2$—$CF(CF_3)$O—$CF_2CF_2$—$SO_2F$ (perfluoro-3,6-dioxa-4-methyl-7-octenesulfonyl fluoride), its corresponding acid, salts, or amides;

$CF_2$=CF—O—$CF_2$—$CF(CF_3)$O—$CF_2CF_2$—COOR" (ester, preferably methyl ester, of perfluoro-4,7-dioxa-5-methyl-8-nonenoic acid), its corresponding acid, salts, or amides;

$CF_2$=CF—O—$CF_2CF_2$—$SO_2F$ (perfluoro-3-oxa-4-pentenesulfonyl fluoride), its corresponding acid, salts, or amides;

$CF_2$=CF—O—$CF_2CF_2$—COOR" (ester, preferably methyl ester, of perfluoro-4-oxa-5-hexenoic acid), its corresponding acid, salts, or amides;

$CF_2$=CF—O—$CF_2$—$CF(CF_3)$—$CF_2CF_2$—$CH_2OH$ (9,9-dihydro-9-hydroxy-perfluoro(3,6-dioxa-5-methyl-1-nonene));

$CF_2$=CF—O—$CF_2CF_2CF_2$—$CH_2OH$ (7,7-Dihydro-7-hydroxy-perfluoro(3-oxa-1-heptene));

$CF_2$=CF—O—$CF_2$—$CF(CF_3)$—$CF_2CF_2$—$CH2OP(O)$ $(OH)_2$ (9-phosphono-9,9-dihydro-perfluoro(3,6-dioxa-5-methyl-1-nonene));

$CF_2$=CF—O—$CF_2$—$CF(CF_3)$—$CF_2CF_2CN$ (perfluoro-8-cyano-5-methyl-3,6-dioxa-1-octene).

R further represents: (C) alkenyl. Alkenyl means an alkyl group containing at least one site of olefinic unsaturation. It is preferred that there be a single site of olefinic unsaturation and preferably that the olefinic unsaturation be a terminal vinyl group. Alkyl means hydrocarbon group, which may be substituted with halogen and, if so substituted, preferably the halogen is fluorine or chlorine, preferably alkyl is fluoroalkyl, and more preferably is perfluoroalkyl. Alkyl may be linear or branched, or cyclic. Preferably, alkyl is linear alkyl. The alkyl group may contain one or more ether linkages. Preferably, the alkyl group has 1 to 20 carbon atoms. These fluorovinyl ethers are preferably trifluorvinyl alkenyl vinyl ethers. Preferred fluorovinyl ethers are perfluoro(alkenyl vinyl ethers). Examples are perfluoro(allyl vinyl ether), perfluoro(3-butenyl vinyl ether); 1,1-dihydro-2,2,3,4,4-pentafluoro-3-butenyl trifluorovinyl ether, and 1,1-dihydroperfluoro-4-pentenyl trifluoro vinyl ether (U.S. Pat. Nos. 4,897,457 and 5,260,492). This class of vinyl ethers can react according to this invention to give disulfonic acids and sulfonates because both the vinyl ether portion of the molecule and the alkenyl group react with sulfite. Members of this class of fluorovinyl ethers are referred to herein as fluoro(alkenyl vinyl ethers).

In each of the classes of R described above, R is said to be fluorinated if at least one of the monovalent atoms bonded to carbon atom in R is a fluorine atom. R is said to be perfluorinated if all of the monovalent atoms bonded to carbon atom in R are fluorine atoms.

The discovery that fluorovinyl ethers can react with sulfite to give hydrofluoroalkanesulfonates makes higher molecular weight, and higher boiling, hydrofluoroalkanesulfonic acids more readily available as well as the corresponding sulfonates. PAVEs are widely used in fluoropolymers of the "PFA" type and commercial facilities for their large scale production are in place. In contrast, higher fluoroolefins, that is fluoroolefins beyond hexafluoropropylene, and especially beyond octafluorobutylene, are not used in fluoropolymers in significant amount, so their availability is limited. Certain functional vinyl ethers and fluoro(alkenyl vinyl ethers) are also the basis of commercial fluoropolymers.

The term sulfite ($SO_3^=$) is used herein with the understanding that in aqueous solution this species is in equilibrium with bisulfite ($HSO_3^-$). This equilibrium may also include sulfurous acid ($H_2SO_3$) and sulfur dioxide ($SO_2$). The ratio of sulfite to bisulfite is a function of the pH of the solution. $SO_3^=/HSO_3^-$ forms a buffer that with proper control can effectively buffer the reaction according to this invention without the introduction of extraneous materials such as borax and phosphate. It is advantageous to avoid extraneous materials because these can be the source of impurities in the product and, in addition, add to the cost of ingredients, increase the variety of chemicals in the waste product, thus increasing the difficulty and cost of disposal or recovery.

The optimum pH range for the formation of hydrofluoroalkanesulfonic acids according to this invention is about 4 to 12, preferably about 5 to 11, more preferably about 5 to 10, and most preferably about 5 to 9. Optimum pH can be attained by adding a sulfite source such as sulfur dioxide ($SO_2$), sulfurous acid, bisulfite, and/or sulfite to water, and adjusting the pH by further addition of a reagent that does not introduce extraneous materials into the reaction. By extraneous material is meant material that is unrelated to the necessary ingredients of the reaction according to this invention. Necessary ingredients are water, sulfite or sulfuric acid. Ingredients that are fugitive in the sense of being easily removed without contamination of the product or residue, such as carbonate, bicarbonate, and or carbon dioxide, are not considered extraneous materials.

Such non-extraneous materials include hydroxide, carbon dioxide ($CO_2$), bicarbonate, carbonate, sulfuric acid, bisulfate, and sulfate, and sulfurous acid, bisulfite, and sulfite. If the initially made solution has too high a pH, one or more of the acidic types of materials listed above, e.g. $SO_2$, sulfuric acid, bisulfate, or $CO_2$ are added. If the initially made solution has too low a pH, one or more of the basic types of materials listed above, e.g. hydroxide, sulfite, or carbonate, are added.

$CO_2$ is a particularly effective reagent. When present, it acts to buffer the reaction and suppress all but the desired product. It is believed that it does this by reacting with hydroxyl ($OH^-$) ion formed in the reaction of sulfite, the effective reactant, with the fluoro(alkyl vinyl ether), as shown in equation (3) below:

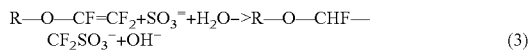

$$R\text{—}O\text{—}CF{=}CF_2 + SO_3^= + H_2O \rightarrow R\text{—}O\text{—}CHF\text{—}CF_2SO_3^- + OH^- \quad (3)$$

One mole of $H_2CO_3$, which is in equilibrium with $CO_2$ in water, reacts with two $OH^-$ to form carbonate ($CO_3^=$), thereby suppressing the reaction of $OH^-$ with vinyl ether to form the acid. Therefore, one mole of $CO_2$ will neutralize $OH^-$ from the reaction of two moles of vinyl ether with $SO_3^=$. Preferably, the mole ratio of vinyl ether to $CO_2$ should be close to the stoichiometric 66:33 (vinyl ether/$CO_2$), such as in the range about 50:50 to about 75:25, more preferably about 60:40 to 70:30, and most preferably about 64:36 to 68:32.

Alternatively, fluorovinyl ether and $CO_2$ may be added in separate streams in the desired ratio, or the $CO_2$ addition may be controlled by means that monitor the reaction solution pH and adjust $CO_2$ addition rate to maintain pH in the desired range.

It is preferred that, for reagents that are ionic, those with alkali metal salts cations be used, preferably the sodium or potassium ion, more preferably the potassium ion. As discussed below, the product of the process will be the hydrofluoroalkanesulfonate salt of the metal ion or ions used in the synthesis.

It is not desirable to have radical initiators, particularly radical initiators capable of initiating the polymerization of fluorovinyl ether present in the reaction mixture and preferably are not employed in the process of the invention. Furthermore, oxygen preferably should be excluded from the reaction vessel, since oxygen is capable of reacting with fluorovinyl ether and may lead to oligomerization. Oxygen can thus cause side reactions that compete with formation of hydrofluoroalkanesulfonic acid, reducing yield and creating useless byproducts that can foul the reactor and cause plugging of lines. In addition, oxygen reacts with sulfite to form sulfate. Since the sulfite concentration is important to controlling the pH of the reaction, such oxidation by oxygen is undesirable.

In the making the hydrofluoroalkanesulfonate according to this invention, a suitable vessel, preferably of stainless steel or other corrosion resistant metal, is charged with aqueous sulfite solution. The solution may be prepared outside the vessel, or made in situ, by charging water and dry ingredients. It is preferred that the water be deionized and oxygen-free. If it is desired to avoid handling dry ingredients, the sulfite solution may be prepared by adding sulfur dioxide ($SO_2$) to aqueous caustic, preferably sodium or potassium hydroxide. pH of the solution should be adjusted to about 4-12. If a sulfite salt, such as sodium or potassium sulfite is the sulfite source, sulfuric acid is a convenient acid for pH adjustment.

After the aqueous sulfite is charged, the vessel is cooled to about 0° C. to −40° C., evacuated and then charged with nitrogen or other inert gas at least once and preferably 2 to 3 times to eliminate oxygen. The vessel is evacuated and then charged with the fluorovinyl ether, closed, and heating is begun. Temperature is raised to about 125° C. and held there with stirring, shaking, or other means of agitating the vessel contents for about 2 to 12 hours. At the end of the reaction time, the vessel is cooled to room temperature, vented, and the contents discharged.

The contents may be concentrated by removal of water, preferably at reduced pressure, preferably in a rotary evaporator. More preferably, water-removal in the rotary evaporator is not carried to the point of dryness. Rather water is further removed by freeze drying. Freeze drying results in a finely divided, easily handled, low moisture solid. Otherwise, the resulting solids tend to be hard and lumpy. The product from the freeze drier preferably contains less than about 5 wt % water, more preferably contains less than about 1 wt % water, and most preferably contains less than about 0.5 wt % water.

Also preferable, is the removal of water by spray-drying the aqueous reaction product.

After water-removal, the solid (crude product) can be further purified by stirring in reagent grade acetone for several hours at room temperature. The product hydrofluoroalkanesulfonate dissolves in acetone, the inorganic salts, such as residual sulfite salts, do not. Filtration of the acetone solution removes undissolved impurities. The acetone solution is then subject to vacuum to remove acetone. The resulting solids, purified hydrofluoroalkanesulfonate salt, can be further dried at low pressure, about 1-20 Pa, at room temperature to remove remaining acetone.

It has been found that on cooling the reactor contents from the reaction of PMVE or PEVE, that the product hydrofluoroalkanesulfonate salt precipitates in high purity (greater than about 98%), leaving little product in the liquid phase. The carboxylic acid salt arising from the reaction shown in equation (2) is more soluble and remains in the liquid phase. When a sufficiently quantitative precipitation of the desired product occurs (this sufficiency will depend on the process economics, including the scale of the process), freeze drying or spray drying of the crude product and acetone purification are preferably omitted.

The product will be the hydrofluoroalkanesulfonate salt of the metal ion or ions used in the synthesis. For example, if potassium sulfite is the source of sulfite, potassium hydrofluoroalkanesulfonate will the product, i.e. potassium ion will be the cation. Potassium is a preferred cation for the hydrofluoroalkanesulfonate salt. If another cation form of the hydrofluoroalkanesulfonate is desired, such as another metal ion, this can be done using ion-exchange or metathetical methods known in the art. The salt can be converted to the acid, i.e. proton (hydrogen ion) is the cation, by reaction with an acid such as by contact with strong acid ion exchange resin, for example, resin made by sulfonating crosslinked polystyrene. For convenience, hydrofluoroalkanesulfonate and the corresponding hydrofluoroalkanesulfonic acid can be represented as a hydrofluoroalkanesulfonate of the formula R—O—CFH—CF$_2$—SO$_3$M, where R is selected from the group consisting of alkyl groups, functionalized alkyl groups, and alkenyl groups, and M is a proton, in which case the molecule is the hydrofluoroalkanesulfonic acid, or other cation, in which case the salt is meant.

A preferred method of acidification is treatment with oleum. This is done after water is removed, but the acetone purification step is not necessary. Acidification may be done on the crude product. It is preferred that the crude product be freeze dried to remove water.

The term "oleum" means H$_2$SO$_4$ containing sulfur trioxide (SO$_3$), preferably in the range of about 1 to 15 wt %. The oleum is preferably used in a weight ratio of at least about 1 part oleum per part dried product. By using oleum, rather than concentrated sulfuric acid, which generally contains from 2-5 wt % water, formation of hydrofluoroalkanesulfonic acid hydrate is avoided. The acid hydrates are often waxy solids at room temperature. They can solidify in the condenser during distillation unless the temperature of the condenser coolant is controlled, which is a burdensome requirement.

Commercially available oleum may have too high an SO$_3$ content. If so, the SO$_3$ concentration can be reduced by mixing the commercial oleum with sulfuric acid. The sulfuric acid addition dilutes the commercial oleum, and water in the sulfuric acid reacts with some of the SO$_3$ to form sulfuric acid. The result is oleum of lower SO$_3$ concentration.

Addition of the oleum gives a slurry, which, on heating in the still, may form a solution, depending on the particular sulfonic acid.

A large excess of oleum is not desirable. It can lead to reduced yields of the sulfonic acid and formation of lower boiling product, believed to be sulfonic acid ester. In the process there should be a small amount, preferably no more than about 5 wt %, more preferably no more than about 3 wt %, most preferably no more than about 1 wt % of low boiling material coming off the distillation before the desired sulfonic acid product. This ensures that no hydrate remains to foul the still. Low boiling material in excess of this is an indication that too much oleum is being used, and the amount should be reduced.

In accordance with a preferred form of the invention which is useful when water is removed by methods other then precipitation in high purity, the resulting solid is preferably converted to the acid form by "directly treating" the solid with oleum. The term "directly treating" with oleum means that no intervening extraction steps are used and the oleum mixed or contacted with the product for treatment. The oleum mixture is then heated to boiling and the product acid distilled off. If the acid is found to be in hydrate form, that is combined with water, stronger oleum or more complete water removal from the product is desirable to avoid additional process steps, such as treatment of the acid hydrate with thionyl chloride to make the unhydrated acid.

Preferred classes of hydrofluoroalkanesulfonate according to this invention are:

MO$_3$S—CF$_2$—CHF—(OCF$_2$CF(CF$_3$))$_n$(O)$_p$(CF$_2$)$_m$—Z, where M is a cation, where p is 0 or 1, m is 0 to 10 and n is 1 to 20, provided that when m is 0, p is 0, and further provided that when m is greater than 0, p is 1, and Z is a functional group such as —CH$_2$OH, carboxyl (—COO$^-$) including carboxylic ester, amide, acid, or salt; sulfonate (—SO$_3^-$) including sulfonyl fluoride, sulfonic acid, sulfonamide, or sulfonate salt; phosphonate (—O—P(O)O$_2^-$), including phosphonic acid, acid halide, or salt; glycidyl; cyanide (—CN); cyanate, and carbamate.

Hydrofluoroalkanesulfonates of the formula MO$_3$S—CF$_2$—CHF—O—Y—CF$_2$—Z, where M is a cation, where Y is alkylene, preferably fluoroalkylene, and more preferably perfluoroalkylene and may be cyclic and may include one or more ether oxygens, and is most preferably CF$_2$, and Z is a functional group such as —CH$_2$OH, carboxyl (—COO$^-$) including carboxylic ester, amide, acid, or salt; sulfonate (—SO$_3^-$) including sulfonyl halide, preferably fluoride, sulfonic acid, sulfonamide, or sulfonate salt; phosphonate (—O—P(O)O$_2^-$), including phosphonic acid, acid halide, or salt; glycidyl; cyanide (—CN); cyanate, and carbamate.

MO$_3$S—CF$_2$—CHF—O—CF$_2$—CF(CF$_3$)O—CF$_2$CF$_2$—SO$_2$M$^1$, where M is a cation and M$^1$ is selected from the group consisting of OH, NR$^1$R$^2$ where R$^1$ and R$^2$ are independently hydrogen or alkyl, and OX, where X is a cation.

MO$_3$S—CF$_2$—CHF—O—CF$_2$—CF(CF$_3$)O—CF$_2$CF$_2$—COM$^1$, where M is a cation and M$^1$ is selected from the group consisting of OH, NR$^1$R$^2$ where R$^1$ and R$^2$ are independently hydrogen or alkyl, and OX, where X is a cation.

MO$_3$S—CF$_2$—CHF—O—CF$_2$CF$_2$—SO$_2$M$^1$, where M is a cation and M$^1$ is selected from the group consisting of OH, NR$^1$R$^2$ where R$^1$ and R$^2$ are independently hydrogen or alkyl, and OX, where X is a cation.

MO$_3$S—CF$_2$—CHF—O—CF$_2$CF$_2$—COM$^1$, where M is a cation and M$^1$ is selected from the group consisting of OH, NR$^1$R$^2$ where R$^1$ and R$^2$ are independently hydrogen or alkyl, and OX, where X is a cation.

MO$_3$S—CF$_2$—CHF—O—CF$_2$—CF(CF$_3$)O—CF$_2$CF$_2$CH$_2$OH. This is derived from

MO$_3$S—CF$_2$—CHF—O—CF$_2$—CF(CF$_3$)O—CF$_2$CF$_2$CN.

MO$_3$S—CF$_2$—CHF—O—CF$_2$—CF(CF$_3$)O—CF$_2$CF$_2$CH$_2$OP(O)(OM)$_2$.

MO$_3$S—CF$_2$—CHF—O—CR$_2$(CF$_2$)$_n$CFHCF$_2$—SO$_3$M.

For hydrofluoroalkanesulfonates with more than one ionic group, the cations need not be identical.

The process as described above may be carried out as a batch process. The process according to this invention may also be run continuously, with continuous or periodic drawing off of the liquid contents of the reactor and continuous or periodic replenishment of reactants.

Salts of the above described hydrofluoroalkanesulfonates useful as photoacid generators or ionic liquids have cations selected from the class, organic onium ions. These include sulfonium and iodonium, such as triphenyl sulfonium and diphenyl iodonium, preferred for photoacid generators, as well as ammonium, phosphonium, bromonium, chloronium and arsonium, among others.

In making the salts starting with the acid, R—O—CXH—CX$_2$—SO$_3$H, the acid may be reacted with a silver salt, e.g., silver carbonate, to form the silver salt of the sulfonic acid, R—O—CXH—CX$_2$—SO3Ag. This silver salt is then reacted with, for example, [(R$^1$)(R$^2$)(R$^3$)S$^+$]X$^-$ or [(R$^4$)(R$^5$)I$^+$] X$^-$(where X=Cl, Br, or I) to form insoluble AgX and the desired onium cation. Y$^+$R$_f$SO$_3^-$.

A preferred method is direct reaction of the potassium salt, R—O—CXH—CX$_2$—SO$_3$K, with, for example, (R$^1$)(R$^2$)(R$^3$)S$^+$X— or (R$^4$)(R$^5$)I$^+$X$^-$(X=Br, Cl, I) to form insoluble MX and the desired sulfonium or iodonium salt, R—O—CXH—CX$_2$—SO$_3$M. This method obviates the need for forming the acid, and can give materials of high purity, e.g., less than 10 ppm of metals that might be deleterious to photolithography processes.

In selected embodiments of this invention, M is triphenylsulfonium or tris(4-t-butylphenyl)sulfonium.

For convenience, is referred to herein as sulfonium or iodonium. In the structures above, $R^1$, $R^2$, $R^3$, $R^4$, and $R^5$ each independently represent an alkyl group, a monocyclic or bicyclic alkyl group, a phenyl group, a naphthyl group, an anthryl group, a peryl group, a pyryl group, a thienyl group, an aralkyl group, or an arylcarbonylmethylene group; or any two of $R^1$, $R^2$, and $R^3$ or $R^4$ and $R^5$ together represent an alkylene or an oxyalkylene which forms a five- or six-membered ring together with the interposing sulfur or iodine, said ring being optionally condensed with aryl groups, one or more hydrogen atoms of $R^1$, $R^2$, $R^3$, $R^4$, and $R^5$ being optionally substituted by one or more groups selected from the group consisting of a halogen atom, an alkyl group, a cyclic alkyl group, an alkoxy group, a cyclic alkoxy group, a dialkylamino group, a dicyclic dialkylamino group, a hydroxyl group, a cyano group, a nitro group, an aryl group, an aryloxy group, an arylthio group, and groups of formulas I to V:

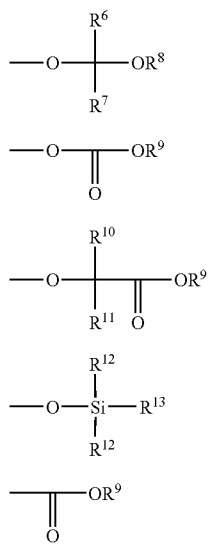

wherein $R^6$ and $R^7$ each independently represent a hydrogen atom, an alkyl group, which may be substituted by one or more halogen atoms, or a cyclic alkyl group, which may be substituted by one or more halogen atoms, or $R^6$ and $R^7$ together can represent an alkylene group to form a ring, $R^8$ represents an alkyl group, a cyclic alkyl group, or an aralkyl group, or $R^6$ and $R^8$ together represent an alkylene group which forms a ring together with the interposing —C—O— group, the carbon atom in the ring being optionally substituted by an oxygen atom, $R^9$ represents an alkyl group or a cyclic alkyl group, one or two carbon atoms in the alkyl group or the cyclic alkyl group being optionally substituted by an oxygen atom, an aryl group, or an aralkyl group, $R^{10}$ and $R^{11}$ each independently represent a hydrogen atom, an alkyl group or a cyclic alkyl group, $R^{12}$ represents an alkyl group, a cyclic alkyl group, an aryl group, or an aralkyl group, and $R^{13}$ represents an alkyl group, a cyclic alkyl group, an aryl group, and aralkyl group, the group —Si($R^{12}$)$_2$ $R^{13}$, or the group —O—Si($R^{12}$)$_2$ $R^{13}$.

The binders useful as photoresist resins for this invention comprise any polymer that has the transparency properties suitable for use in microlithography. It is contemplated that binders suitable for the present invention may include those polymers that are typically incorporated into chemically amplified 248 (deep UV) and 193 nm photoresists for imaging at longer wavelengths. A typical 248 nm photoresist binder is based on polymers of para-hydroxystyrene. Other examples of suitable 248 nm photoresist binders can be found in the reference *Introduction to Microlithography*, Second Edition by L. F. Thompson, C. G. Willson, and M. J. Bowden, American Chemical Society, Washington, D.C., 1994, chapter 3. Binders useful for 193 nm photoresists include cycloolefin-maleic anhydride alternating copolymers [such as those disclosed in F. M. Houlihan et al., *Macromolecules*, 30, pages 6517-6534 (1997); T. Wallow et al., *Proc. SPIE*, 2724, 355; and F. M. Houlihan et al., *Journal of Photopolymer Science and Technology*, 10, 511 (1997)], polymers of functionalized norbornene-type monomers prepared by metal-catalyzed vinyl addition polymerization or ring-opening metathesis polymerization [such as those disclosed in U. Okoroanyanwu et al. J. Mol. Cat A: *Chemical* 133, 93 (1998), and PCT WO 97/33198], and acrylate copolymers [such as those described in U.S. Pat. No. 5,372,912]. Photoresist binders that are suitable for use with this invention also include those which are transparent at wavelengths below 248 and 193 nm such as those polymers containing fluoroalcohol functional groups [such as those disclosed in K. J. Pryzbilla et al. *Proc. SPIE* 1672, 9 (1992), and H. Ito et al. *Polymn. Mater. Sci. Eng.* 77, 449 (1997)].

Typical examples of polymers that are also useful are those that have been developed for use in chemically amplified photoresists which are imaged at an irradiation wavelength of 157 nm. Examples of such polymers are fluoropolymers and fluoropolymers containing fluoroalcohol functional groups. Suitable examples have been disclosed in WO 00/17712 and WO 00/25178.

The quantity of polymeric binder in the photoresist composition may be in the amount of about 50 to about 99.5 weight % based on the weight of the total photoresist composition (solids).

A photoresist composition in accordance with the invention contains a combination of polymeric binder and photoactive component, i.e., organic onium hydrofluoroalkanesulfonate. The photoactive compound may be present in the amount of about 0.5 to about 10% by weight typically about 1 to about 5% by weight, based on the total dry weight of photoresist composition.

Various dissolution inhibitors can be utilized in th photoresist composition in accordance with the invention. Ideally, dissolution inhibitors (DIs) for the far and extreme UV photoresists (e.g., 193 nm photoresists) are selected to satisfy multiple needs including dissolution inhibition, plasma etch resistance, and adhesion behavior of photoresist compositions comprising a given DI additive. Typically, a dissolution inhibitor is included in a photoresist composition to assist in the development process. A good dissolution inhibitor will inhibit the unexposed areas of the photoresist layer from dissolving during the development step in a positive working system. A useful dissolution inhibitor may also function as a plasticizer which function provides a less brittle photoresist layer that will resist cracking. These features are intended to improve contrast, plasma etch resistance, and adhesion behavior of photoresist compositions.

Some dissolution inhibiting compounds may also serve as plasticizers in photoresist compositions.

A variety of bile-salt esters (i.e., cholate esters) are particularly useful as dissolution inhibitors in the compositions of this invention. Bile-salt esters are known to be effective dissolution inhibitors for deep UV photoresists, beginning with work by Reichmanis et al. in 1983. (E. Reichmanis et al., "The Effect of Substituents on the Photosensitivity of 2-Nitrobenzyl Ester Deep UV Resists", *J. Electrochem. Soc.* 1983, 130, 1433-1437.) Bile-salt esters are particularly attractive choices as dissolution inhibitors for several reasons, including their availability from natural sources, their possessing a high alicyclic carbon content, and particularly for their being transparent in the deep and vacuum UV region, (which essentially is also the far and extreme UV region), of the electromagnetic spectrum (e.g., typically they are highly transparent at 193 nm). Furthermore, the bile-salt esters are also attractive dissolution inhibitor choices since they may be designed to have widely ranging hydrophobic to hydrophilic compatibilities depending upon hydroxyl substitution and functionalization.

Representative bile-acids and bile-acid derivatives that are suitable as dissolution inhibitors for this invention include, but are not limited to, those illustrated below, which are as follows: cholic acid (IV), deoxycholic acid (V), lithocholic acid (VI), t-butyl deoxycholate (VII), t-butyl lithocholate (VII), and t-butyl-3-α-acetyl lithocholate (IX). Bile-acid esters, including compounds VII-IX, are preferred dissolution inhibitors in this invention.

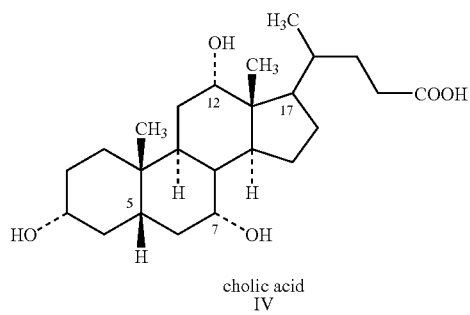

cholic acid
IV

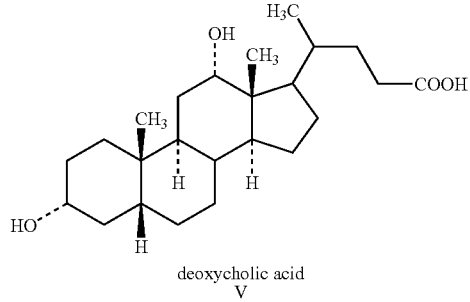

deoxycholic acid
V

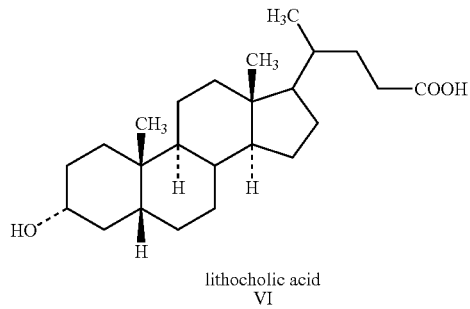

lithocholic acid
VI

-continued

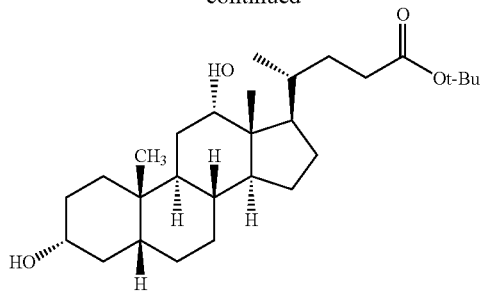

t-butyl deoxycholate
VII

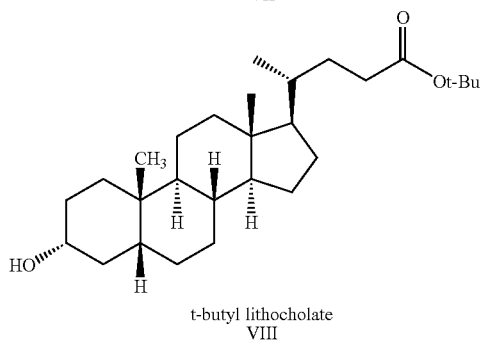

t-butyl lithocholate
VIII

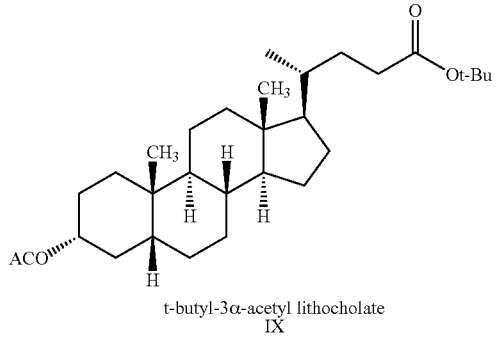

t-butyl-3α-acetyl lithocholate
IX

The quantity of dissolution inhibitor in the photoresist composition may range from about 0.5 to about 50 wt % based on the total weight of the solids in the photoresist composition.

The compositions of this invention can contain optional additional components. Examples of additional components which can be added include, but are not limited to, resolution enhancers, adhesion promoters, residue reducers, coating aids, plasticizers, and $T_g$ (glass transition temperature) modifiers. Crosslinking agents may also be present in negative-working photoresist compositions. Some typical crosslinking agents include bis-azides, such as, 4,4'-diazidodiphenyl sulfide and 3,3'-diazidodiphenyl sulfone. Typically, a negative working composition containing at least one crosslinking agent also contains suitable functionality (e.g., unsaturated C=C bonds) that can react with the reactive species (e.g., nitrenes) that are generated upon exposure to UV to produce crosslinked polymers that are not soluble, dispersed, or substantially swollen in developer solution.

The photoresist composition can include an amount of solvent, typically an organic solvent such as cyclohexanone. The solvent is usually used in an amount sufficient to dissolve the binder and the photoactive component. A specific solvent found to be useful is cyclohexanone.

The process for forming a photoresist image on a substrate comprises, in order:

(A) imagewise exposing a photoresist layer to form imaged and non-imaged areas, wherein the photoresist layer is prepared from a photoresist composition comprising:

(a) a polymeric binder; and (b) a photoactive component selected from photoacid generators, $Y^{+R}_f SO_3^-$, as described above;

(B) developing the exposed photoresist layer having imaged and non-imaged areas to form the relief image on the substrate.

The photoresist layer is prepared by applying a photoresist composition onto a substrate and drying to remove the solvent. The photoresist layer is, typically, applied by spin coating onto a substrate, typically a silicon wafer having a primer applied thereon. The so formed photoresist layer is sensitive in the ultraviolet region of the electromagnetic spectrum and especially to those wavelengths ≦365 nm. Imagewise exposure of the photoresist compositions of this invention can be done at many different UV wavelengths including, but not limited to, 365 nm, 248 nm, 193 nm, 157 nm, and lower wavelengths. Imagewise exposure is preferably done with ultraviolet light of 248 nm, 193 nm, 157 nm, or lower wavelengths, preferably it is done with ultraviolet light of 193 nm, 157 nm, or lower wavelengths, and most preferably, it is done with ultraviolet light of 157 nm or lower wavelengths. Imagewise exposure can either be done digitally with a laser or equivalent device or non-digitally with use of a photomask. Digital imaging with a laser is preferred. Suitable laser devices for digital imaging of the compositions of this invention include, but are not limited to, an argon-fluorine excimer laser with UV output at 193 nm, a krypton-fluorine excimer laser with UV output at 248 nm, and a fluorine ($F_2$) laser with output at 157 nm. Since, as discussed supra, use of UV light of lower wavelength for imagewise exposure corresponds to higher resolution (lower resolution limit), the use of a lower wavelength (e.g., 193 nm or 157 m or lower) is generally preferred over use of a higher wavelength (e.g., 248 nm or higher). After exposure, the wafer is usually baked to increase or decrease the ability of exposed areas of the photoresist to be removed in developer. The photoresist compositions of this invention must contain sufficient functionality for development following imagewise exposure to UV light. Preferably, the functionality is an acid or protected acid such that aqueous development is possible using a basic developer such as sodium hydroxide solution, potassium hydroxide solution, or ammonium hydroxide solution, such as tetramethylammonium hydroxide.

When an aqueous processible photoresist is coated or otherwise applied to a substrate and imagewise exposed to UV light, development of the photoresist composition may require that the binder material should contain sufficient acid groups (e.g., fluoroalcohol groups) and/or protected acid groups that are at least partially deprotected upon exposure to render the photoresist (or other photoimageable coating composition) processible in aqueous alkaline developer. In case of a positive-working photoresist layer, the photoresist layer will be removed during development in portions which are exposed to UV radiation but will be substantially unaffected in unexposed portions during development by aqueous alkaline liquids such as wholly aqueous solutions containing 0.262 N tetramethylammonium hydroxide (with development at 25° C. usually for less than or equal to 120 seconds). In case of a negative-working photoresist layer, the photoresist layer will be removed during development in portions which are unexposed to UV radiation but will be substantially unaffected in exposed portions during development using either a critical fluid or an organic solvent.

A critical fluid, as used herein, is one or more substances heated to a temperature near or above its critical temperature and compressed to a pressure near or above its critical pressure. Critical fluids in this invention are at least at a temperature that is higher than 15° C. below the critical temperature of the fluid and are at least at a pressure higher than 5 atmospheres (500 kPa) below the critical pressure of the fluid. Carbon dioxide may be used for the critical fluid in the present invention. Various organic solvents can also be used as developer in this invention. These include, but are not limited to, halogenated solvents and non-halogenated solvents. Halogenated solvents are typical and fluorinated solvents are more typical.

The substrate employed in this invention can be any material used in semiconductor manufacture, for example, a wafer usually made from silicon, silicon oxide, silicon nitride and the like. Usually, a primer is applied to the silicon wafer. A typical primer composition is hexamethyldisilazane.

EXAMPLES

Glossary

Analytical/Measurements bs broad singlet
δ NMR chemical shift measured in the indicated solvent
g gram
NMR Nuclear Magnetic Resonance
$^1$H NMR Proton NMR
$^{19}$F NMR Fluorine-19 NMR
s singlet
sec. second(s)
m multiplet
mL milliliter(s)
mm millimeter(s)
$T_g$ Glass Transition Temperature
$M_n$ Number-average molecular weight of a given polymer
$M_w$ Weight-average molecular weight of a given polymer
$P=M_w/M_n$ Polydispersity of a given polymer
Absorption coefficient AC=A/b, where A, absorbance, =$Log_{10}$ (1/T) and b=film thickness in microns, where T=transmittance as defined below.
Transmittance Transmittance, T, =ratio of the radiant power transmitted by a sample to the radiant power incident on the sample and is measured for a specified wavelength λ (e.g., nm).

Chemicals/Monomers

HAdA Hydroxyadamantyl acrylate (2-Propenoic acid, 3-hydroxytricyclo[3.3.1.13,7]dec-1-yl ester) [CAS registry number 216581-76-9] (Idemitsu Chemical USA, Southfield, Mich.)
MAdA 2-Methyl-2-adamantyl acrylate (2-propenoic acid, 2-methyltricyclo[3.3.1.13,7]dec-2-yl ester) [CAS Registry number 249562-06-9] (Idemitsu Chemical USA, Southfield, Mich.)
PinAc 2-Propenoic acid, 2-hydroxy-1,1,2-trimethylpropyl ester [CAS Reg number 97325-36-5]
TFE Tetrafluoroethylene E. I. du Pont de Nemours and Company, Wilmington, Del.
THF Tetrahydrofuran Sigma-Aldrich Chemical Co., St. Louis, Mo.
NB—F—OH X=$OCH_2C(CF_3)_2OH$ NB—F—OH was prepared as described by Feiring and Feldman, PCT Int. Appl. WO 2000067072 (11/9/2000).

Ultraviolet

Extreme UV Region of the electromagnetic spectrum in the ultraviolet that ranges from 10 nanometers to 200 nanometers Far UV Region of the electromagnetic spectrum in the ultraviolet that ranges from 200 nanometers to 300 nanometers UV Ultraviolet region of the electromagnetic spectrum which ranges from 10 nanometers to 390 nanometers Near UV Region of the electromagnetic spectrum in the ultraviolet that ranges from 300 nanometers to 390 nanometers Unless otherwise specified, all temperatures are in degrees Celsius, all mass measurements are in grams, and all percentages are weight percentages.

Unless otherwise indicated, n, appearing within structure(s) given in the examples, represents the number of repeat units in the polymer. Throughout the specification, p, appearing within structure(s), represents the number of repeat units in the polymer.

Glass transition temperatures ($T_g$) were determined by DSC (differential scanning calorimetry) using a heating rate of 20° C./min, data is reported from the second heat. The DSC unit used is a Model DSC2910 made by TA Instruments, Wilmington, Del.

The term "clearing dose" indicates the minimum exposure energy density (e.g., in units of $mJ/cm^2$) to enable a given photoresist film, following exposure, to undergo development.

Unless otherwise indicated, all reagents were obtained from Sigma-Aldrich Co. (St. Louis, Mo.).

Example 1

Synthesis of Potassium 1,1,2-Trifluoro-2-(trifluoromethoxy)ethanesulfonate (TTES-K) and 1,1,2-Trifluoro-2-(trifluoromethoxy)ethanesulfonic acid This example demonstrates the reaction of perfluoro(methyl vinyl ether) (PMVE) according to this invention. A 400 ml Hastelloy® C276 reaction vessel is charged with a solution of 11.4 g potassium bisulfite hydrate ($KHSO_3 \cdot H_2O$, 95%, Aldrich, 0.07 mol), 44.5 g potassium metabisulfite ($K_2S_2O_5$, 99%, Mallinckrodt, 0.20 mol) and 200 ml of deionized water. The pH of this solution is 5.8. The vessel is cooled to −35° C., evacuated to −3 psig (80.6 kPa), and purged with nitrogen. The evacuate/purge cycle is repeated two more times. To the vessel is then added 60 g perfluoro(methyl vinyl ether) (PMVE, 0.36 mol). The vessel is heated to 125° C. at which time the internal pressure is 571 psig (4040 kPa). The reaction temperature is maintained at 125° C. for 4 hr. The pressure drops to 33 psig (330 kPa) at which point the vessel is vented and cooled to 25° C. The reaction product is a clear light yellow reaction solution of pH 7.0, and a precipitate The crude reaction product is placed in a freeze dryer (Virtis Freezemobile 35 xl) for 72 hr to reduce the water content to approximately 0.5 wt. % (117 g). The theoretical mass of total solids is approximately 119 g. The crude product is stirred with 800 ml of reagent grade acetone for 4 hr at 25° C. The product dissolves, the undissolved inorganic salts are removed by filtration through a fritted glass funnel. The acetone is removed in vacuo and the remaining solid is dried at 30 milliTorr (4 Pa) at 25° C. for 3 hours to remove residual acetone affording 86.7 g (84% yield) of white solid identified (see below) as potassium 1,1,2-trifluoro-2-(trifluoromethoxy)ethanesulfonate (TTES-K).

$^{19}$F NMR ($D_2O$)δ −59.9 d, $^3J_{FH}$=4 Hz, 3F); −119.6, −120.2 (subsplit ABq, J=260 Hz, 2F); −144.9 (dm, $^2J_{FH}$=53 Hz, 1 F)

$^1$H NMR ($D_2O$)δ 6.6 (dm, $^2J_{FH}$=53 Hz, 1 H).

% Water by Karl-Fisher titration: 71 ppm.

Analysis calculated for $C_3HF_6SO_4K$: C, 12.6: H, 0.4: N, 0.0 Found: C, 12.6: H, 0.0: N, 0.1.

Melting point (DSC) 257° C.

TGA (air): 10% weight loss at 343° C., 50% weight loss at 358° C.

TGA (nitrogen): 10% weight loss at 341° C., 50% weight loss at 375° C.

A 100 ml round bottom flask with a sidearm is equipped with a digital thermometer and a magnetic stirbar and placed in an ice bath under positive nitrogen pressure. To the flask is added 60 g crude TTES-K from the previous step along with 35 g of concentrated sulfuric acid (EM Science, 95-98%) and 95 g oleum (Acros, 20 wt % SO3) while stirring. This amount of oleum is chosen so that the SO3 reacts with and removes the water in the sulfuric acid as well as in the crude TTES-K while still being present in slight excess. The mixing causes a small exotherm which is controlled by the ice bath. Once the exotherm is over, a distillation head with a water condenser is placed on the flask and it is heated under nitrogen behind a safety shield. The pressure is slowly reduced using a PTFE membrane vacuum pump (Buchi V-500) in steps of 100 Torr (13 kPa) in order to avoid foaming. A dry-ice trap is also placed between the distillation apparatus and the pump to collect any excess $SO_3$. The flask is heated and the pressure is held at 20-30 Torr (2.7-4.0 kPa). The flask contents begin to reflux and then distill. A forerun of lower-boiling impurity (approximately 2 g) is obtained before collecting 30 g of the colorless liquid, which by NMR analysis is found to have a spectrum consistent with that of the expected acid, 1,1,2-trifluoro-2-(trifluoromethoxy)ethanesulfonic acid.

Example 2

Synthesis of Potassium 1,1,2-Trifluoro-2-(trifluoromethoxy)ethanesulfonate (TTES-K)

A 1-gallon Hastelloy C276 reaction vessel is charged with a solution of 114 g potassium sulfite hydrate ($KHSO_3 \cdot H2O$, 95%, Aldrich, 0.72 mol), 440 g potassium metabisulfite ($K_2S_2O_5$, 99%, Mallinckrodt, 1.98 mol) and 2000 mL of deionized water. The pH of this solution is 5.8. The vessel is cooled to −35° C., evacuated to −3 psig (81 kPa), and purged with nitrogen. This evacuate/purge cycle is repeated two more times. 600 g perfluoro(methyl vinyl ether) (PMVE, 3.61 mol) is added to the vessel, which is heated to 125° C. at which time the internal pressure is 462 psig (3290 kPa). The reaction temperature is maintained at 125° C. for 6 hr. The pressure drops to 25 psig (275 kPa) at which point the vessel is vented and cooled to 25° C. Once cooled, a white crystalline precipitate of the forms, leaving clear colorless liquid above it (pH=7). $^{19}$F NMR of the white solid shows it to be the desired product in high purity (>98%). $^{19}$F NMR of the liquid shows a small but detectable amount of the hydration product of Equation (3), above.

The liquid and precipitate are slurried and suction filtered through a fritted glass funnel for 6 hr to remove most of the water. The wet cake is then dried in a vacuum oven at 100 Torr (13 kPa) and 50° C. for 48 hr. This gives 854 g (83% yield) of a white powder. The final product is pure (by $^{19}$F and $^1$H NMR) since the undesired hydration product (Equation (2))

remains in the water during filtration. The aqueous layer is freeze-dried to afford 325 g of material.

Analysis: calculated for $C_3HF_6SO_4K$: C, 12.6: H, 0.4: N, 0.0 Found: C, 12.3: H, 0.7: N, 0.0.

This example shows that the desired adduct precipitates in good yield at high purity. It can be used without further purification. Little of the adduct remains in the liquid layer (<17%).

Example 3

Synthesis of Potassium 1,1,2-Trifluoro-2-(perfluoroethoxy)ethanesulfonate (TPES-K)

A 1-gallon reaction vessel made of Hastelloy C276 is charged with a solution of 88 g potassium sulfite hydrate ($KHSO_3·H_2O$, 95%, Aldrich, 0.56 mol), 340 g potassium metabisulfite ($K_2S_2O_5$, 99%, Mallinckrodt, 1.53 mol) and 2000 mL of deionized water. The vessel is cooled to 7° C., evacuated to −7 psig (48 kPa), and purged with nitrogen. The evacuate/purge cycle is repeated two more times. To the vessel is then added 600 g perfluoro(ethyl vinyl ether) (PEVE, 2.78 mol) and the vessel is heated to 125° C. at which time the inside pressure is 320 psig (2300 kPa). The reaction temperature is maintained at 125° C. for 10 hr. The pressure drops to 23 psig (260 kPa) at which point the vessel is vented and cooled to 20° C. The crude reaction product is a white crystalline precipitate with a colorless aqueous layer (pH=7) above it.

19F NMR of the white solid shows pure desired product. 19F NMR of the aqueous layer shows a small but detectable amount of the hydration product shown in Equation (3).

The desired compound ($C_2F_5O$—$CF_2H$—$CF_2$—$SO_3^{-K+}$) is less soluble in water so it precipitates in pure form.

The product slurry is suction filtered through a fritted-glass funnel. The wet cake is dried in a vacuum oven (60° C., 100 Torr (13 kPa)) for 48 hr. The product is obtained as off-white crystals (904 g, 97% yield).

$^{19}F$ NMR ($D_2O$) δ −86.5 (s, 3F); −89.2, −91.3 (subsplit ABq, $^2J_{FF}$=147 Hz, 2F); −119.3, −121.2 (subsplit ABq, $^2J_{FF}$=258Hz, 2F); −144.3 (dm, $^2J_{FH}$=53 Hz, 1 F).

$^1H$ NMR ($D_2O$) δ 6.7 (dm, $^2J_{FH}$=53 Hz, 1 H).

Melting point (DSC) 263° C.

Elemental Analysis calculated for $C_4HO_4F_8SK$: C, 14.3: H, 0.3 Found: C, 14.1: H, 0.3.

TGA(air): 10% weight loss at 359° C. 50% weight loss at 367° C. TGA($N_2$): 10% weight loss at 362° C, 50% weight loss at 374° C.

NMR analysis of the liquid phase shows it to contain about 3% of the undesirable hydration product (Equation (3)).

Compared to the adduct of Example 2, the higher molecular weight adduct of PEVE is less soluble and therefore precipitates in higher yield, obviating the need for further purification or further recovery of whatever small amount remains in the liquid phase.

Example 4

Synthesis of Adduct of Sodium Bisulfite and Lithium Perfluoro-3.6-dioxa-4-methyl-7-octenesulfonate Example 4 shows the reaction of a functional vinyl ether. In this case the product has a sulfonate group at both ends.

1. Synthesis of lithium salt of perfluoro-3,6-dioxa-4-methyl-7-octenesulfonyl fluoride (PDMOF)

The reaction can be represented as:

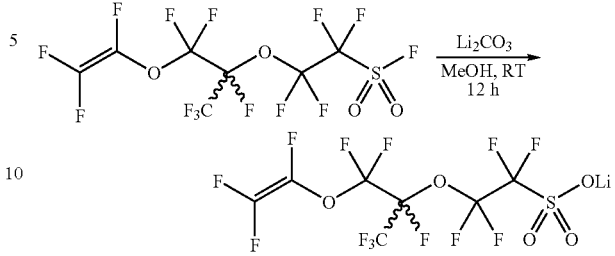

To a 2-neck 50 mL flask is added 1.66 g (0.02 mol) lithium carbonate (Aldrich, >99%) and 10 mL dry methanol. The system is purged with nitrogen and cooled to 7° C. using an ice bath. PDMOF (10.0 g, 0.02 mol) is added dropwise via glass syringe over 20 minutes. No exotherm is observed during this addition. The solution is allowed to warm to room temperature (20-25° C.) and stirred for 12 hr. Reaction is monitored by $^{19}F$ NMR and is complete when the signal for the fluorine bonded to sulfur (+43.4 ppm) is no longer observed.

The reaction solution is filtered through a 0.4 micron Teflon® PTFE syringe filter to remove the lithium fluoride precipitate as well as any remaining lithium carbonate. The methanol is removed in vacuo (60 mTorr (8 Pa), 25°C., 4 hr) to give 10 g of a waxy solid. The product still contains some methanol.

2. Reaction of Li-PMDOF with Sodium sulfite/bisulfite

The reaction can be represented as:

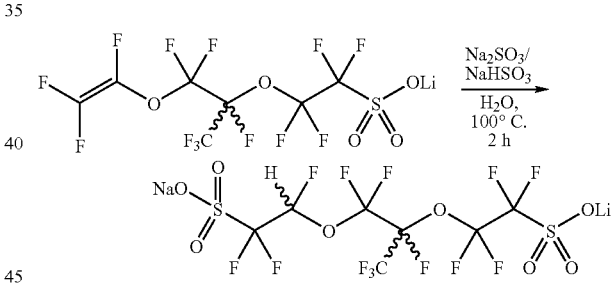

To a 100 mL flask is added 10 g of Li-PMDOF (0.02 mol), 2.3 sodium bisulfite (0.02 mol), 0.6 g sodium sulfite (4.4 mmol), and 40 mL deionized water. This mixture is stirred and heated to reflux for 2 hr using an oil bath. An $^{19}F$ NMR ($D_2O$) spectrum of the solution at this point shows complete conversion by the absence of any vinyl fluorine signals. The aqueous solution (pH=7) is reduced in vacuo to give the crude product as a white solid. The solid is dissolved in 50 mL of spectrophotometric grade acetone (Aldrich) and stirred magnetically for 12 hr. A small amount of insoluble material (~2 g) is removed by suction filtration and the remaining acetone is removed in vacuo to give 12.0 g (0.22 mol) of white solid (97% yield).

Analysis. Calculated for $C_7HO_8S_2F_{13}NaLi$: C, 15.2: H, 0.2, N, 0.0, Found: C, 15.0: H, 1.2: N, 0.2.

Melting pt. (DSC) 135° C.

TGA (air): 10% weight loss at 360° C., 50% weight loss at 411° C.

TGA (nitrogen): 10% weight loss at 356° C., 50% weight loss at 394° C.

DSC is differential scanning calorimetry.
TGA is thermal gravimetric analysis.

Example 5

Synthesis of Triphenylsulfonium-1,1,2-trifluoro-2-(perfluoroethoxy)ethanesulfonate (TPS-TPES)

TPS-TPES, potassium-1,1,2-trifluoro-2-(perfluoroethoxy)ethanesulfonate (29.4 g, 8.74×10$^{-2}$ mol), is dissolved in 600 mL of deionized water at room temperature (RT) in a 1000 mL flask. In a separate 500 mL flask, 30.0 g (8.74×10$^{-2}$ mol) of triphenylsulphonium bromide (TPS-Br, DayChem Inc., Dayton, Ohio) is dissolved in 220 mL deionized water at 40° C. These two solutions are combined and stirred at RT for 3 hr, at which point the product is observed as a light yellow oil on the bottom of the flask. The oil is removed and washed with 2×100 mL portions of deionized water. It is then dried in vacuo at 75 milliTorr (10 Pa) and 40° C. for 1 hr, and then at 60 milliTorr (8 Pa) and 25° C. for 5 hr. The product is in the form of a light yellow oil (42.3 g, 86% crude yield). The product crystallized as a white solid from this oil over the period of several days (34.0 g, 69% yield).

$^{19}$F NMR (d$_6$-DMSO) δ −87.4 (s, 3F); −89.5, −91.8 (subsplit ABq, $J_{FF}$=147 Hz, 2F); −122.4, −124.0 (subsplit ABq, $J_{FF}$=253 Hz, 2 F); −143.9 (dm, $J_{FH}$=54 Hz, 1 F). $^1$H NMR (d6-DMSO) δ 6.5 (dt, J=54 Hz, J=7 Hz, 1 H); 7.8 (m, 15 H).

Carbon Hydrogen (elemental) analysis: Found: C, 46.7: H, 2.7. melting point (DSC) =74.9° C.

The results of the NMR and elemental analysis show the product to be triphenylsulfonium-1,1,2-trifluoro-2-(perfluoroethoxy)ethanesulfonate (TPS-TPES).

Example 6

Synthesis of Triphenylsulfonium-1,1,2-trifluoro-2-(trifluoromethoxy)ethanesulfonate (TPS-TTES)

TPS-TTES, potassium-1,1,2-trifluoro-2-(trifluoromethoxy)ethanesulfonate, (25.0 g, 8.74×10$^{-2}$ mol) is dissolved in 200 mL of deionized water in a 500 mL flask. In a separate 500 mL flask, 30.0 g (8.74×10$^{-2}$ mol) of triphenylsulfonium bromide (TPS-Br, DayChem Inc.) is dissolved in 200 mL deionized water. These solutions are heated to 40° C. with stirring for 15 min to dissolve the solids. The two solutions are mixed while still warm, which resulted in an immediate milky white suspension as well as a light brown oil. This mixture is stirred for 16 hr at RT. The oil is separated and the colorless aqueous (pH=4) layer is extracted with methylene chloride (3×100 mL). The product oil is combined with the methylene chloride washes and this organic layer is further washed with 50 mL of saturated sodium carbonate and then 50 mL of deionized water. This layer is dried over magnesium sulfate and reduced in vacuo to afford 43.7 g of a yellow oil (98% crude yield). The desired product slowly crystallized from the oil to give a white crystalline solid.

$^{19}$F NMR (CD$_3$CN, ref. CFCl$_3$) δ −58.8d, $J_{FH}$=4 Hz, 3 F); −121.6 (m, 2 F); −143.6 (dm, $J_{FH}$=54 Hz, 1 F).

$^1$H NMR (CD$_3$CN) δ 6.4 (dt, $J_{HF}$=7 Hz, $J_{HF}$=54 Hz, 1 H); 7.8 (m, 15 H). Carbon Hydrogen (elemental) Analysis: C, 49.0: H, 3.0. melting point (DSC) 63.7° C.

The results of the NMR and elemental analysis show the product to be triphenylsulfonium-1,1,2-trifluoro-2-(trifluoromethoxy)ethanesulfonate (TPS-TTES).

Example 7

Photoresist Prepared from a TPS-TPES Photoacid Generator (PAG)

A. Synthesis of TFE/NB-F-OH/PinAc/HAdA/MAdA Pentapolymer

A 4000 mL pressure vessel is charged with 695.4 g (2.398 mol) of NB—F—OH, 25.1 g (0.146 mol) of PinAc, 77.4 g (0.282 mol) of HAdA, 10.7 g (0.049 mol) of MAdA, 60.4 g (0.840 mol) of THF and 381.6 g (2.578 mol) of Solkane® 365 mfc. The vessel is closed and heated to 50° C. under agitation at 100 rpm. The vessel is then charged with TFE until the reactor pressure reached 180 psig (1.24 MPa), at which point about 86 g (0.860 mol) of TFE is expected to be in the solution at that pressure and temperature. The monomer composition at the beginning of the run, then, is targeted to be 23% TFE, 64% NB—F—OH, 4% PinAc, 8% HadA, and 1% MAdA (mol %) and the reactor contained 1336 g of solution, including dissolved TFE. When the reaction temperature and pressure setpoints are reached, continuous flow of three solutions to the reactor is begun. Two of these solutions contained the monomers and chain transfer agent (THF) and the third contained the initiator. The first monomer solution contained 711.9 g (2.455 mol) of NB—F—OH, 51.6 g (0.717 mol) of THF and 125.4 g (0.847 mol) of Solkane® 365mfc. This solution is metered into the reactor by means of an Isco series D high-pressure precision syringe pump at a constant rate of 1.054 g/min for 720 min. The second monomer solution contained 122.8 g (0.714 mol) of PinAc, 378.1 g (1.380 mol) of HAdA, 52.3 g (0.238 mol) of MAdA, 49.0 g (0.681 mol) of THF, 119.1 g (0.805 mol) of Solkane® 365mfc and 171.4 g (2.301 mol) of methyl acetate to aid in dissolution of the monomers. This solution is metered in a second Isco series D high-pressure precision pump at a constant rate of 1.088 g/min for 720 min. The initiator solution contained 89.2 g (0.224 mol) of Perkadox® 16N, 369.7 g (2.498 mol) of Solkane® 365mfc and 518.9 g (7.012 mol) of methyl acetate. The initiator solution is metered into the reactor with an Isco series D high-pressure precision syringe pump at 35.49 g/min for six min, followed by a rate of 1.42 g/min for 480 min. TFE is supplied to the reactor over the course of 720 min by maintaining the reactor pressure at 180 psig (1.34 MPa). The calculated total amounts of ingredients added to the vessel after 720 min of reaction is 275.7 g (2.757 mol) of TFE, 1287.9 g (4.441 mol) of NB-F-OH, 132.3 g (0.769 mol) of PinAc, 407.5 g (1.487 mol) of HAdA, 56.4 g (0.256 mol) of MAdA, 146.2 g (2.031 mol) of THF, 922.9 g (6.236 mol) of Solkane® 365mfc, 602.3 g (8.139 mol) of methyl acetate and 81.6 g (0.205 mol) of Perkadox® 16N. The reaction temperature is held at 50° C., the pressure is maintained with TFE feed at 180 psig (1.34 MPa), and the agitation rate is 100 rpm over the course of the 720 min of reaction. After 720 min, the TFE feed is stopped and the reactor is held under agitation for 4 hr at 50° C. The vessel is then cooled rapidly to room temperature and vented to 1 atmosphere. The vessel contents are transferred to a container via blowcasing after adding an additional 400 ml of THF to reduce viscosity and aid in rinsing of the vessel. A 1073.4 g (890 ml) sample of the resultant polymer solution is metered into a 22-L agitated flask containing 16020 ml of n-heptane (18/1 volume ratio to polymer solution). After mixing for 30 min, the slurry is discharged across an in-line cloth filter. The wet precipitate on the filter weighed 497.8 g. A sample of this precipitate (478.7 g.) is redissolved with 765.9 ml of Solkane® 365mfc and 480 ml of THF. The resultant solution is precipitated a second time into a vessel containing n-heptane at a volume ratio of 18/1 with the polymer solution. After mixing for 30 min, the slurry is discharged again across another in-line cloth filter. The filtrate is dried under vacuum with a nitrogen bleed at 70° C. for 16 hr to obtain 347 g of very fine, white powder. Gel permeation chromatography of the product indicated Mn=5130, Mw=9780 and Mw/Mn=1.91. A combination of $^{13}C$ and $^{19}F$ NMR analyses of the product resulted in a calculated polymer composition of 15 mol % TFE, 39 mol % NB—F—OH, 10 mol % PinAc, 30 mol % HAdA and 6 mol % MAdA.

B. The following formulation is prepared and magnetically stirred overnight:

| Component | Wt. (gm) |
|---|---|
| TFE/NB—F—OH/PinAc/MAdA/HAdA Polymer (15/39/10/6/30) | 2.95 |
| 2-Heptanone | 20.63 |
| Tetrabutylammonium lactate solution prepared by diluting a 1% (wt) solution of tetrabutylammonium hydroxide solution in ethyl lactate (2.5 gm 40% (wt) aqueous tetrabutylammonium hydroxide + 97.5 gm ethyl lactate) with an equal weight of 2-heptanone | 0.72 |
| 6.82 wt % solution of photoacid generator TPS-TPES from Example 3 dissolved in 2-heptanone that had been filtered through a 0.45 µm PTFE syringe filter. | 0.88 |

The wafer is prepared by applying a hexamethyldisilazane (HMDS) primer layer using a YES-3 vapor prime oven. A 100% HMDS adhesion promoter from Arch Chemical Co. is used. The oven is set to give a prime at 150° C. for 300 seconds.

The sample is spin coated using a Brewer Science Inc. Model-100 CB combination spin coater/hotplate on a 4" (100 mm) diameter Type "P", <100> orientation, silicon wafer. To prepare the coating, 2 ml of the above solution, after filtering through a 0.45 µm PTFE syringe filter, is deposited and spun at 1500 rpm for 60 sec, and then baked at 150° C. for 60 sec.

248 nm imaging is accomplished by exposing the coated wafer to light obtained by passing broadband UV light from an ORIEL Model-82421 Solar Simulator (1000 watt) through a 248 nm interference filter which passes about 30% of the energy at 248 nm. Exposure time is 15 sec, providing an unattenuated dose of 3 mJ/cm2. By using a mask with 18 positions of varying neutral optical density, a wide variety of exposure doses are generated. After exposure, the exposed wafer is baked at 135° C. for 60 sec.

The wafer is tray-developed for 60 sec in aqueous 2.38 wt % tetramethylammonium hydroxide (TMAH) solution (LDD-26W, Rohm & Haas Electronics, Marlborough, Mass.). This test generates a positive image with a clearing dose of 5.8 mJ/cm$^2$.

Example 8

Photoresist Prepared from a TPS-TTES

Photoacid Generator (PAG)

A formulation is prepared as in Example 7, except that the photoacid generator used is that (TPS-TTES) prepared in Example 4. This test generates a positive image with a clearing dose of 4.9 mJ/cm$^2$.

What is claimed is:

1. A compound of the formula R—O—CXH—CX$_2$—SO$_3$M, where R is selected from the group consisting of alkyl groups, functionalized alkyl groups, and alkenyl groups; X is selected from the group consisting of hydrogen and fluorine with the proviso that at least one X is fluorine; and M is cation.

2. The compound of claim 1 wherein R is fluorinated.

3. The compound of claim 1 wherein R is perfluorinated.

4. The compound of claim 1 wherein said cation is potassium.

5. Hydrofluoroalkanesulfonates of the formula MO$_3$S—CF$_2$—CHF—(OCF$_2$CF(CF$_3$))$_n$(O)$_p$(CF$_2$)$_m$—Z, where M is a cation, where p is 0 or 1, m is 0 to 10 and n is 1 to 20, provided that when m is 0, p is 0, and further provided that when m is greater than 0, p is 1, and Z is a functional group selected from the group consisting of —CH$_2$OH, carboxyl (—COO$^-$) including carboxylic ester, amide, acid, or salt; sulfonate (—SO$_3^-$) including sulfonyl halide, sulfonic acid, sulfonamide, or sulfonate salt; phosphonate (—O—P(O)O$_2^-$), including phosphonic acid, acid halide, or salt; glycidyl; cyanide (—CN); cyanate, and carbamate.

6. Hydrofluoroalkanesulfonates of the formula MO$_3$S—CF$_2$—CHF—O—Y—CF$_2$—Z, where M is a cation, where Y is selected from the group consisting of alkylene, fluoroalkylene, and perfluoroalkylene and may be cyclic and may include one or more ether oxygens, and Z is a functional group selected from the group consisting of —CH$_2$OH, carboxyl (—COO$^-$) including carboxylic ester, amide, acid, or salt; sulfonate (—SO$_3^-$) including sulfonyl halide, sulfonic acid, sulfonamide, or sulfonate salt; phosphonate (—O—P(O)O$_2^-$), including phosphonic acid, acid halide, or salt; glycidyl; cyanide (—CN); cyanate, and carbamate.

7. A compound of the formula R—O—CXH—CX$_2$—SO$_3$M, where R is selected from the group consisting of alkyl groups, functionalized alkyl groups, and alkenyl groups; X is selected from the group consisting of hydrogen and fluorine with the proviso that at least one X is fluorine; and M is organic onium.

8. The compound of claim 7 wherein M is selected from the group consisting of organic sulfonium and organic iodonium.

9. The compound of claim 7 wherein M is selected from the group consisting of triphenylsulfonium and tris(4-t-butylphenyl)sulfonium.

* * * * *